(12) United States Patent
Alden

(10) Patent No.: US 9,599,589 B2
(45) Date of Patent: Mar. 21, 2017

(54) METHOD FOR SENSING ARRIVAL AND MONITORING FLOW OF A SAMPLE IN A TESTING DEVICE

(71) Applicant: Sanofi-Aventis Deutschland GmbH, Frankfurt am Main (DE)

(72) Inventor: Don Alden, Sunnyvale, CA (US)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 154 days.

(21) Appl. No.: 14/637,246

(22) Filed: Mar. 3, 2015

(65) Prior Publication Data

US 2015/0346142 A1    Dec. 3, 2015

Related U.S. Application Data

(63) Continuation of application No. 12/640,446, filed on Dec. 17, 2009, now abandoned.

(60) Provisional application No. 61/141,159, filed on Dec. 29, 2008.

(51) Int. Cl.
     *G01N 27/327*      (2006.01)
     *G01N 27/416*      (2006.01)

(52) U.S. Cl.
     CPC ..... *G01N 27/4163* (2013.01); *G01N 27/3274* (2013.01)

(58) Field of Classification Search
     CPC ..................................... G01N 27/327–27/3278
     USPC ..... 204/403.01–403.15; 205/777.5–778, 792
     See application file for complete search history.

(56) References Cited

U.S. PATENT DOCUMENTS

| | | | |
|---|---|---|---|
| 2005/0072670 A1* | 4/2005 | Hasegawa | C12Q 1/006 204/403.01 |
| 2007/0017824 A1* | 1/2007 | Rippeth | G01N 27/3272 205/792 |
| 2007/0205114 A1* | 9/2007 | Mathur | G01N 27/3274 205/792 |

* cited by examiner

*Primary Examiner* — Bach Dinh
(74) *Attorney, Agent, or Firm* — Paul Davis; Beyer Law Group

(57) ABSTRACT

A method is provided for sensing arrival and monitoring flow of a sample in a testing device. A meter relay is provided for sensing a sample arrival in the testing device that includes three electrodes for measurement of an analyte in a sample that includes a switch located in an analog or digital part of a circuit, the testing device including a reference electrode lead, a counter electrode lead, and a working electrode lead.

14 Claims, 18 Drawing Sheets

METHOD FOR SENSING ARRIVAL AND MONITORING FLOW OF A SAMPLE IN A TESTING DEVICE

CROSS-REFERENCE TO RELATED APPLICATIONS

This application is a continuation of U.S. patent application Ser. No. 12/640,446, filed Dec. 17, 2009, now abandoned which claims the benefit of U.S. Ser. No. 61/141,159 filed Dec. 29, 2008. This application is also related to commonly owned PCT/IB05/02351 filed May 24, 2005. Both applications are fully incorporated herein by reference.

BACKGROUND

Field of the Invention

This invention relates generally to methods for determining the actual surface area of an electrode, and more particularly to methods for the determination of the real electrochemical surface area of a working electrode of a screen printed sensor.

Description of the Related Art

The actual surface area of an electrode where electron exchange takes place is termed the real or active electrochemical surface area. It is different from the geometrical surface area which is simply the sum of all the physical areas that cover the surface of the electrode. The ratio of the electrochemical surface to the geometrical surface is represented by the roughness factor (p) as a coefficient. In general, the active area of an electrode exceeds the geometrical surface area creating a higher number of chemically reactive sites on comparatively small electrodes. Most of the kinetic parameters of the electrode reaction as well as the electrical double layer properties need to be referred to the unit area. Therefore, the determination of the real surface area of the electrodes plays a crucial role in the calculation of various parameters characterizing electrochemical processes and facilitates quality control of mass produced electrodes.

Various electrochemical methods to determine the real surface area of conventional solid electrode (e.g. carbon electrodes and metal electrodes) have been reported. Methods have been reported for the determination of real electrochemical surface area of liquid electrodes. By contrast, however, the determination of the real electrochemical surface area of screen-printed electrodes still remains underdeveloped, due to the inherently physical properties of screen-printed electrodes. For example, the surface of the screen-printed carbon electrodes is not as smooth as some conventional electrodes such as glassy carbon electrodes and pyrolytic graphite electrodes. Thus, some electrochemical methods are inapplicable to the real surface area determination of screen-printed electrodes where the good surface condition is required. In addition, there are some other hindrances such as the complexity and non-uniformity of the materials and production procedures for screen-printed electrodes. To the best of our knowledge, no effective method has previously been reported for the real electrochemical surface area determination of screen-printed electrodes.

Accordingly, there is a need for methods that determine the real electrochemical surface area of screen-printed electrodes.

SUMMARY

An object of the present invention is to provide methods for determining the real electrochemical surface area of screen-printed electrodes.

Another object of the present invention is to provide methods for determining the real surface area of the electrodes in order to determine various parameters characterizing electrochemical processes.

Still another object of the present invention is to provide methods for determining the real surface area of electrodes to ascertain the concentration range of the detected analytes.

A further object of the present invention is to provide methods for determining the real electrochemical surface area of screen-printed electrodes using chronocoulometry.

Yet another object of the present invention is to provide methods for determining the real electrochemical surface area of screen-printed electrodes by relying on the Anson equation which defines the charge time dependence for linear diffusion control.

Still a further object of the present invention is to provide methods for determining the real electrochemical surface area of screen-printed electrodes by calculating a diffusion coefficient and an unknown concentration of the mediator incorporated in a working electrode paste.

These and other objects of the present invention are achieved in, a method for determining a real electrochemical surface area of a working electrode (WE) of a screen printed sensor. A concentration of a mediator incorporated in a WE paste is determined. The diffusion coefficient of the mediator is then ascertained. A final real electrochemical surface area of the WE is then made.

DETAILED DESCRIPTION

Figure 1:
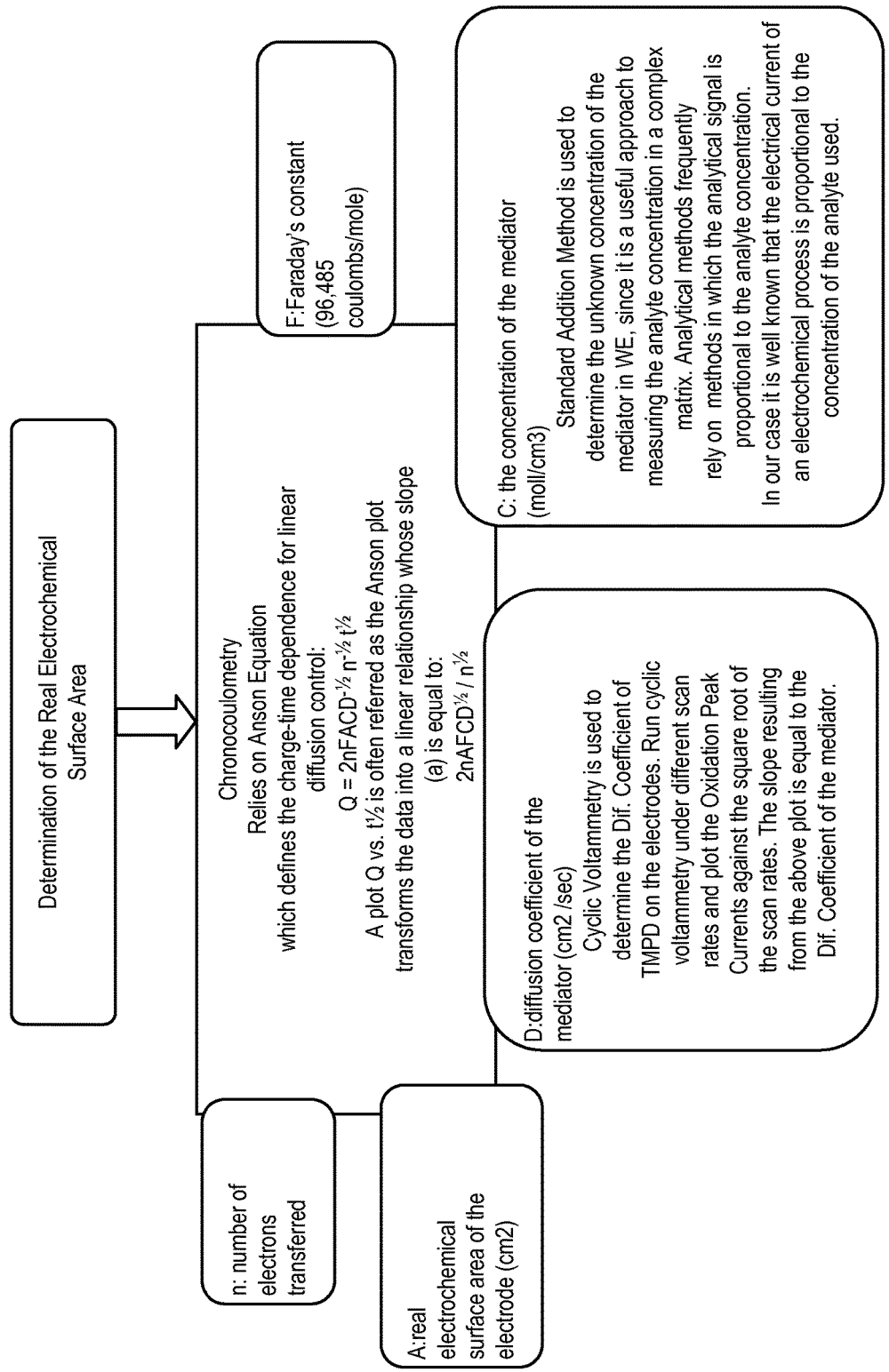
FIG. 1 is an overall flowchart illustrating one embodiment of the present invention for determining the real area of the electrochemical surface area of a working electrode.
Figure 2:
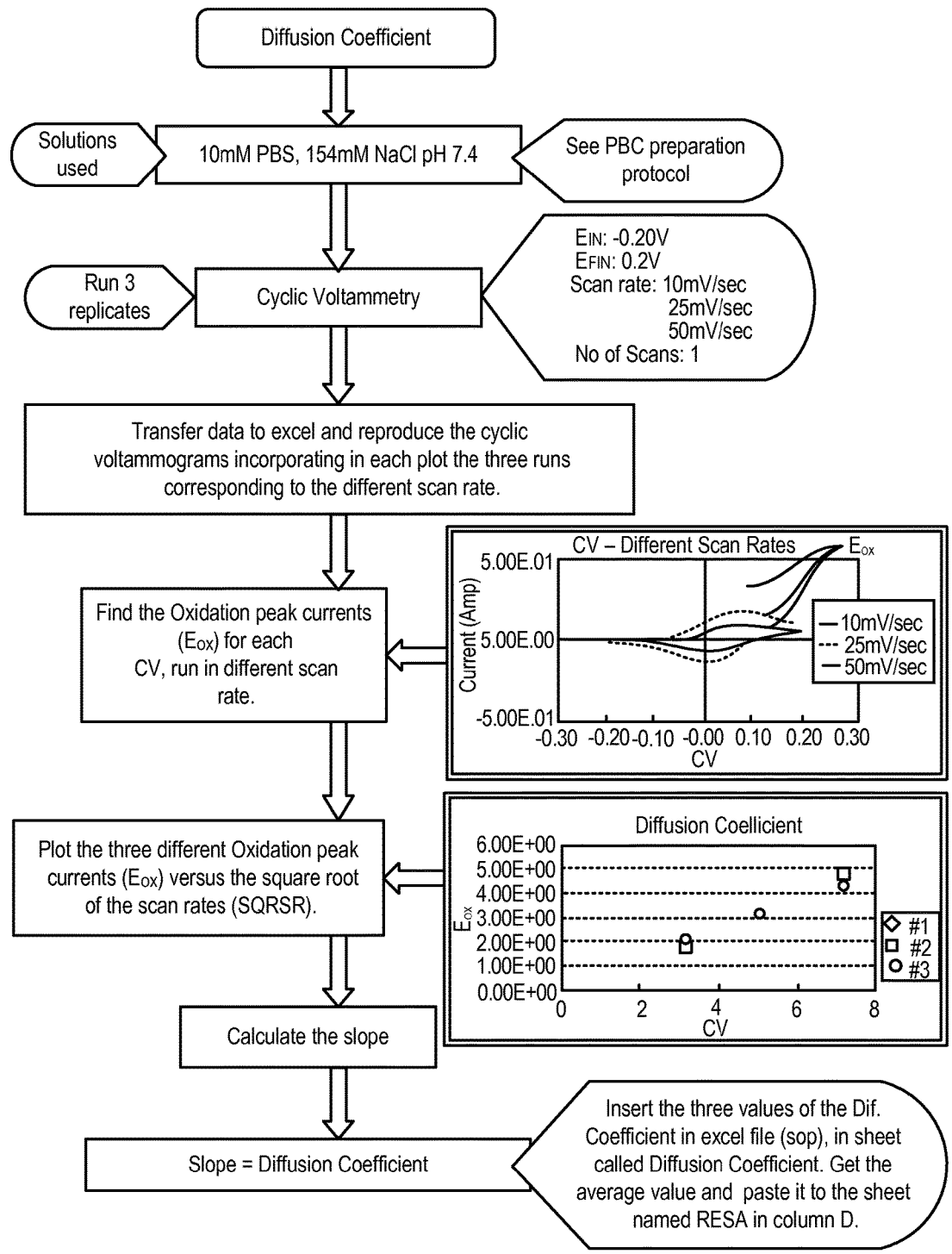
FIG. 2 is a flowchart illustrating one embodiment of the diffusion coefficient used with the FIG. 1 embodiment.
Figure 3:
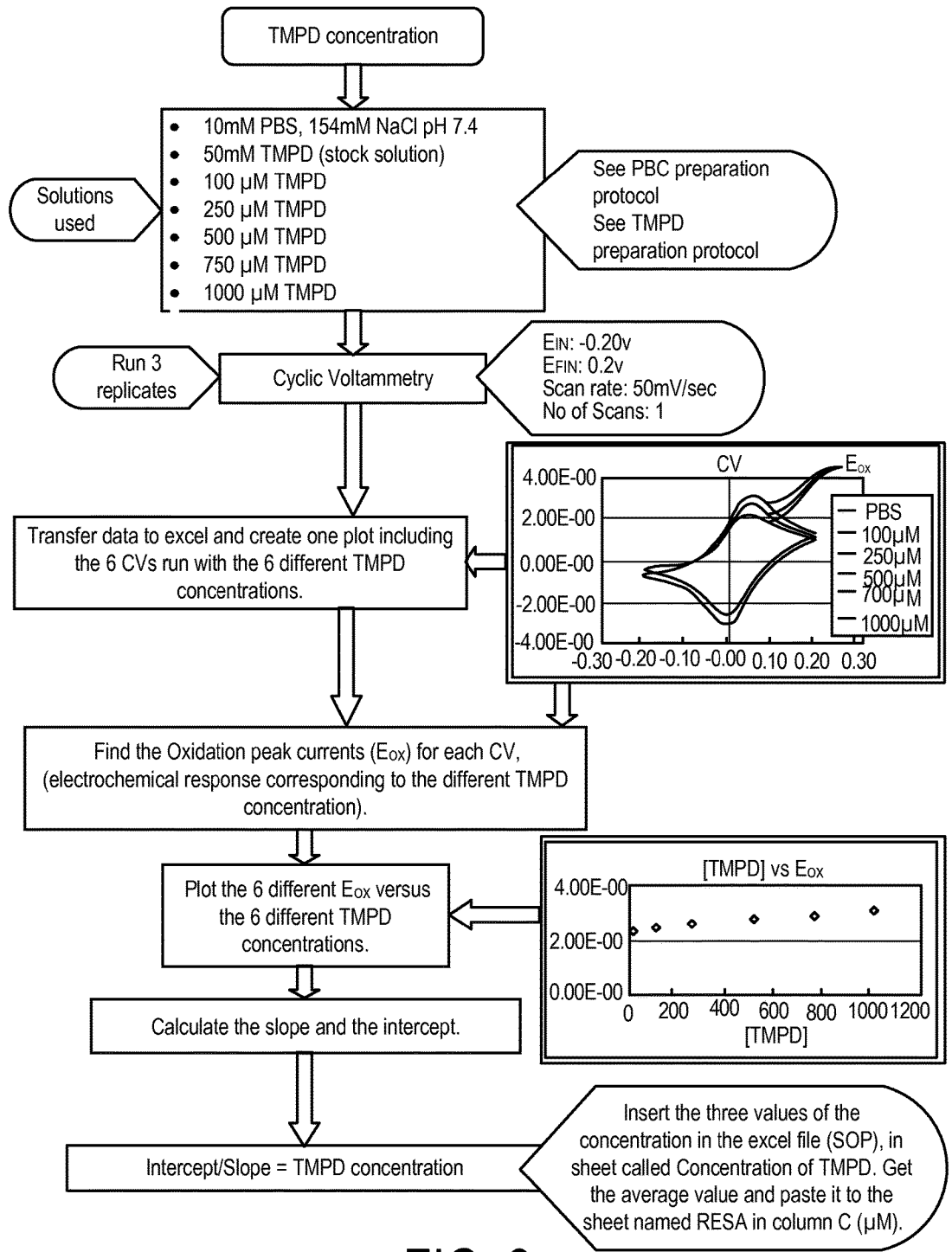
FIG. 3 is a flow chart illustrating one embodiment of the TMPD concentration used with the FIG. 1 embodiment.
Figure 4:
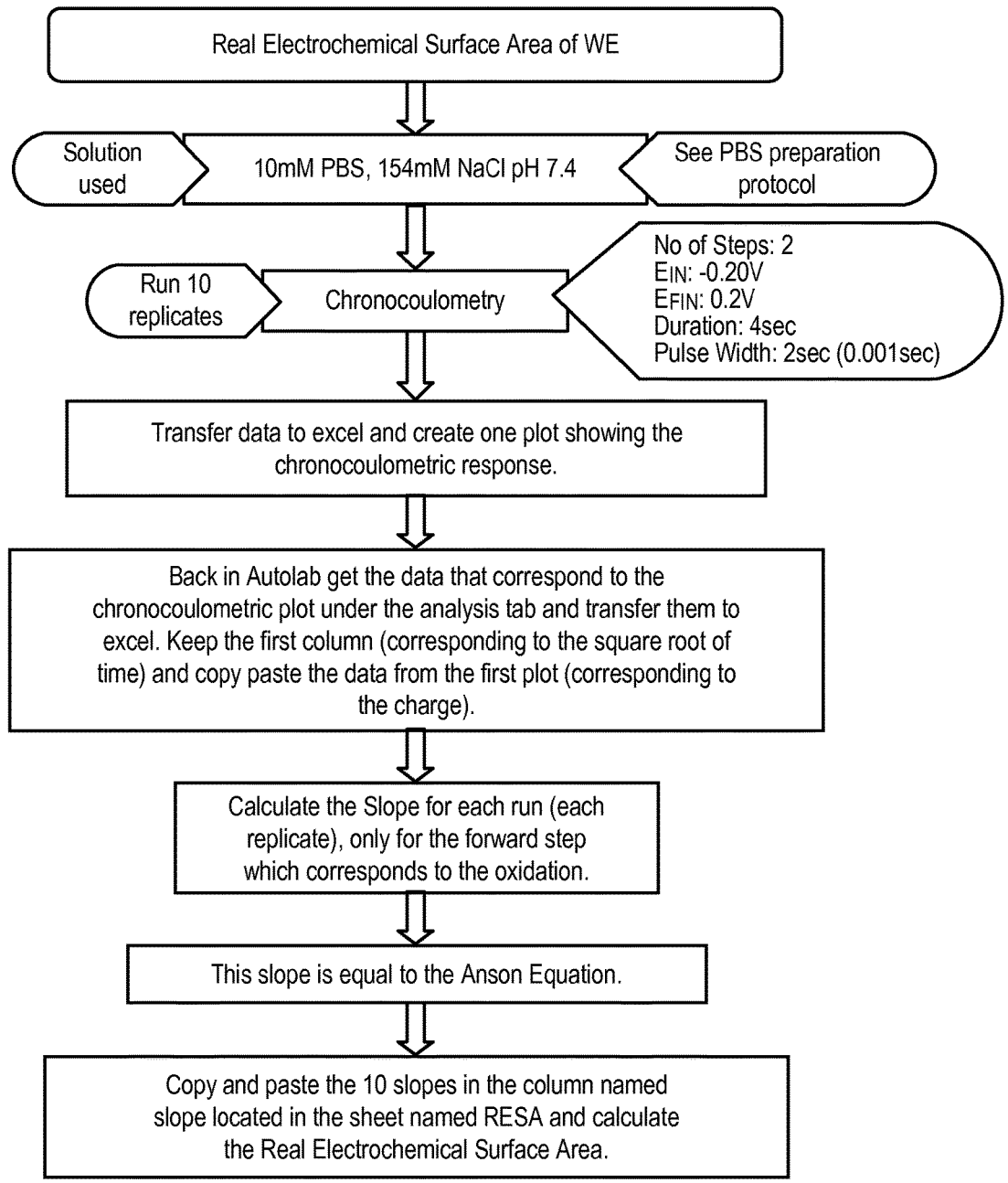
FIG. 4 is a flow chart illustrating one embodiment of the real electrochemical surface area of the working electrode of the present invention.

Referring to FIGS. 1-4, in one of embodiment of the present invention, a method is provided for determining the real surface area of a screen-printed WE using chronocoulometry. In one embodiment, the WE is used in an analyte detecting system, such as one to determine a concentration of glucose in the blood. Chronocoulometry relies on the Anson equation which defines the charge time dependence for linear diffusion control. The Anson plot transforms the data into a linear relationship whose slope is equal to $2nAFCD^{1/2}/\pi^{1/2}$ The Anson plot is a plot of Q vs. $t^{1/2}$ and transforms data into a linear relationship whose slope (a) is equal to:

$$2nAFCD^{1/2}/_{\pi}{}^{1/2}$$

where:
Q is the charge (coulombs);
n is the number of electrons transferred;
A is the real electrochemical surface area of the WE ($cm^2$);
F is Faraday's constant (96,485 coulombs/mole);
C is the concentration of the mediator ($moll/cm^3$) and
D is a diffusion coefficient of the mediator ($cm^2/sec$).

By calculating the diffusion coefficient and the unknown concentration of the mediator incorporated in the WE paste, and by rearranging the above equation, it is possible to determine the real electrochemical surface area of the WE of a screen printed sensor.

The method of the present invention facilitates determination of the real surface area of screen-printed WE's and provides better functionality, as well as providing an improvement of a sensor.

In one embodiment, a method is provided for determining a real electrochemical surface area of a WE of a screen printed sensor. The WE paste can be a complex matrix structure containing both conducting elements and assay reagents.

A determination or calculation is made of a concentration of a mediator incorporated in a WE paste. This determination can include running cyclic voltammetry, and applying a standard addition method. In one embodiment, different solutions of mediator with different concentrations in PBS are prepared, and cyclic voltammograms are then run to observe an (Eox) of the WE after applying increased concentrations of mediator on the WE. A specific electrochemical response corresponds to an added concentration of the mediator as well as of an unknown concentration of the mediator present in the WE paste. Oxidation peak currents observed in the cyclic voltammograms ("CVs") can be plotted against a concentration of the added mediator. After calculating a slope and an intercept of the oxidation peak currents, the unknown concentration of the mediator is calculated by dividing the intercept with the slope.

In one embodiment, the concentration of the mediator incorporated in the WE paste is unknown. A calculation or determination is made of the diffusion coefficient of the mediator. A determination or calculation is then made of the final real electrochemical surface area of the WE. As a non-limiting example, the screen printed sensor can be a three electrode system that includes, two printed carbon electrodes acting as a WE and counter electrode, and a printed Ag/AgCl reference electrode.

In one embodiment, the calculation of the diffusion coefficient of the mediator includes first running cyclic voltammetry under three different scan rates to create electrode cyclic voltammograms, and then plotting oxidation peak currents against a square root of scan rates. In one embodiment, PBS is run on the electrode cyclic voltammograms under three different scan rates to obtain three different oxidation peak currents that correspond to the different scan rates. In one embodiment, the slope of the plot of the three oxidation peak currents (Eox) plotted against the square root of the scan rates is equal to a diffusion coefficient of the mediator.

Chronocoulometry can be used to determine the real electrochemical surface area of the WE. Chronocoulometry is a measurement of charge as a function of time, wherein an analysis of chronocoulometric data is based on an Anson equation that defines a charge-time dependence for linear diffusion control:

$$Q=2nFACD_{1/2}\pi_{T1/2}t-1/2 2CD$$

where:
Q is the charge (coulombs);
n is the number of electrons transferred;
A is the real electrochemical surface area of the WE ($cm^2$);
F is Faraday's constant (96,485 coulombs/mole);
C is the concentration of the mediator;
D is a diffusion coefficient of the mediator ($cm^2/sec$): and
t is time (sec).

EXAMPLE 1

In order to use the above equation is necessary to know the concentration of the mediator in the WE paste as well as the diffusion coefficient of the mediator. To calculate the diffusion coefficient of the mediator, cyclic voltammetry was employed. By applying PBS on the electrode cyclic voltammograms were run in three different scan rates (10 mV/sec, 25 mV/sec and 50 mV/sec). Three oxidation peak currents (Eox) were then plotted against the square root of the scan rates. The obtained slope of the above plot is equal to the diffusion coefficient of the mediator.

In order to calculate the unknown concentration of the mediator the standard addition method was used. Five different solutions of TMPD were used with different concentrations (100 µM, 250 µM, 500 µM, 750 µM and 1000 µM) in PBS and cyclic voltammograms were run in order to observe the (Eox) of the WE after applying increased concentrations of mediator on the WE. The specific electrochemical response corresponded to the added concentration of the mediator as well as of the unknown concentration of the mediator present in the WE paste. In order to observe the electrochemical response of the sensor, which corresponds only to the concentration of the mediator present in the WE paste, cyclic voltammograms were run with plain PBS. The oxidation peak currents observed in the CVs were then plotted against the concentration of the added mediator. After calculating the slope and the intercept of the above plot the unknown concentration of the mediator was determined by dividing the intercept with the slope.

The final values of the diffusion coefficient and TMPD concentration used in the Anson equation were the average value of three replicates.

In one embodiment, the present invention provides optimized signal to background noise designs. Current ratio of signal to background optimization can use one of the following to obtain improved results: 1) use of a hydrogel with zwitterionic compounds or 2) changes in hydrophilic layer dimensions to obtain improved signaling" Currently available test strips have a maximum signal to noise ratio of about 20. Experimental data for analyte detecting devices with and without hydrophilic layer and with/without zwitterionic compound illustrates that the present invention can achieve significantly improved signal to noise ratio. In other embodiments, the mediator content, geometrical design of the electrode and the sample chamber also influence the signal.

Some embodiments can achieve signal to noise ratio greater than 200 Some embodiments can achieve signal to noise ratio greater than 25. Some embodiments can achieve signal to noise ratio greater than 30. Some embodiments can achieve signal to noise ratio greater than 35. In one embodiment, because the reduced form of the mediator is embedded into the reaction zone of one embodiment of the present analyte detecting device, a current can be observed after applying the voltage. This generates the oxidized form of the mediator, which is able to react with the reduced form of the enzyme glucose oxidase. For this particular example, in the absence of glucose (using phosphate buffered saline only (pH 7.4)) a (background) current, will be detected.

As a nonlimiting example, adding 500 mM glucose in buffer and applying a voltage, the saturation current can be determined. The excess glucose is so that the device is not limited by lack of glucose when making the saturation current measurement. The original background current can be caused by the oxidation of mediator by the electrode. In one embodiment of the present invention, the mediator exists in the reduced form in the carbon paste, and is active in the oxidized form during the measurement.

There is typically always a little reduced mediator present which gives the background signal (which is termed the "glucose independent" current). Approaches to reduce this background current in the art are to try and oxidize the mediator before the measurement most are inefficient at achieving this and so there is a lot of reduced mediator available leading to a larger background current and hence lower Q (in the range of 20).

Chronoamperometric methods look at last section of the graph so that a low amount of reduced mediator is observed, as most of the mediator has disappeared from the electrode paste and does not contribute to background. coulometric methods look at charge generated during the entire reaction. At the start, there is a lot of background signal, and at the end there is little, but the result is the integration over the whole time, resulting in total charge and hence the sum of background signal as a result It is therefore inherently difficult with the coulometric methods to get a high Q. The ratio of y previously, thickness of the hydrogel can also improve signal to noise ratio. It should be understood that chamber dimension and layer thickness might influence the signal Several micrormeters in change to they hydrogel layer can be sufficient to alter the ratio. In one embodiment, the thickness of the layer is about 4 micrometers. Increasing the thickness also increases the ratio. Unfortunately, increased thickness of the layer can also slow the diffusion rate of the analyte.

The slope is the diffusion dependent current, and if a thick hydroptlilic member is used, the diffusion rate of glucose to electrodes is decreased. Number of glucose molecules per second is slower. In some embodiments, the thickness will not exceed 30 micrometers. In other embodiments, the thickness will not exceed 50 micrometers.

Figure 5:
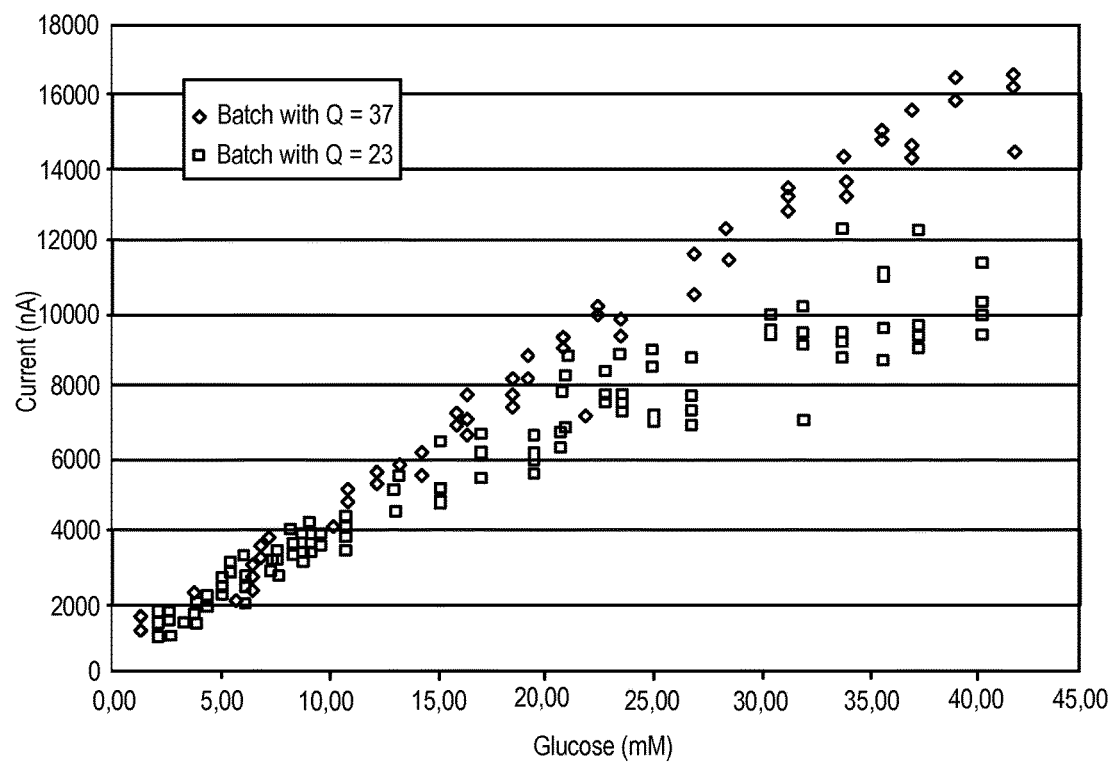
FIG. 5 illustrates a graph of signal to noise ratio.

Referring now to FIG. 5, the importance of a high Q value is reflected in the ability to measure glucose at the higher concentrations. FIG. 5 illustrates the results of glucose concentration versus current for two different batches of test strips, which have components known to generate different values of Q. As seen, the test strip batch having a ratio of 23 has only a measuring range up to 20 mM glucose in whole blood, whereas a batch having a ratio of 37 illustrates a measuring range up to about 40 mM glucose in whole blood.

Both batches have same background. (In one embodiment of the present invention, the background current is about 1 000 nA).

The graph of FIG. 5 confirms the same precision in the low range of glucose, but higher precision in the high range as well as a broader range of glucose concentration measurement at the high glucose levels. At low glucose concentration (2.5 mM) the ratio between the slope and the background is important and the precision is important. Q can be increased by applying (e.g. screen-printing) a hydrophilic membrane over the working electrode.

Figure 6:
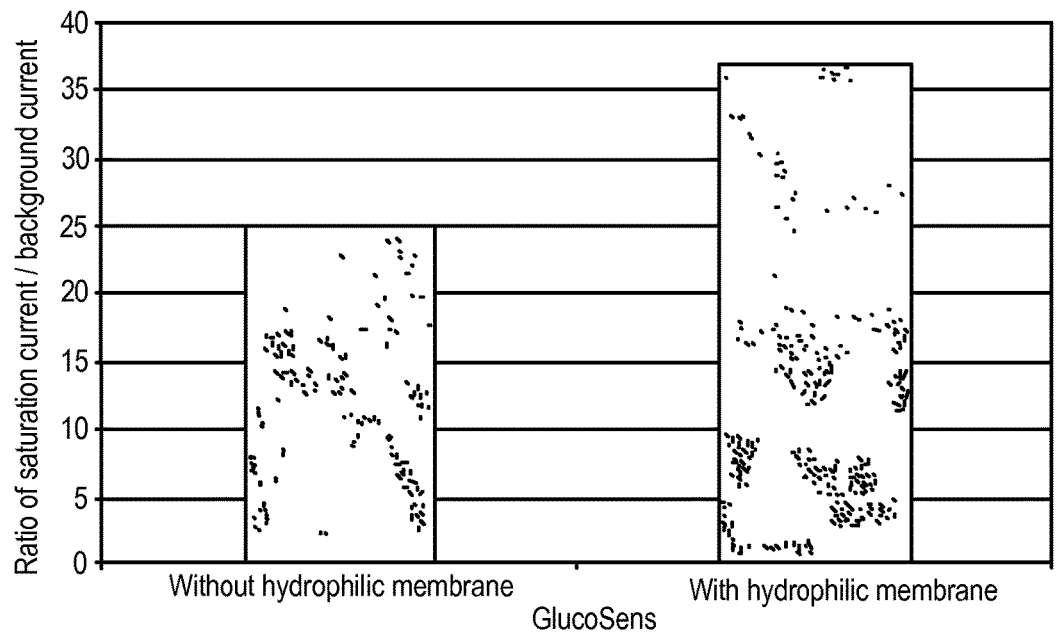
FIGS. 6-8 are charts comparing signal to noise ratios for various embodiments of the present invention.

FIG. 6 illustrates that application of a hydrophilic membrane to the analyte detecting device construction increases Q. The membrane effectively functions by enhancing the concentration of the mediator at the surface of the working electrode. The net result is that the actual concentration of the mediator in the reaction zone is higher in comparison to the batch having no hydrophilic membrane.

Figure 7:
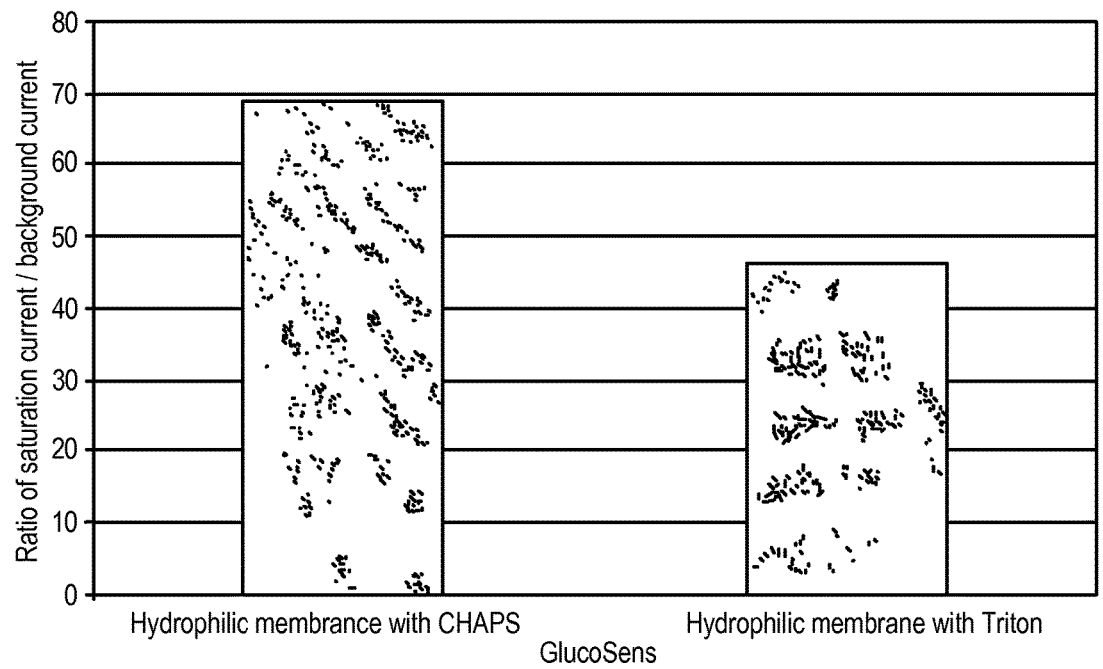
Figure 8:
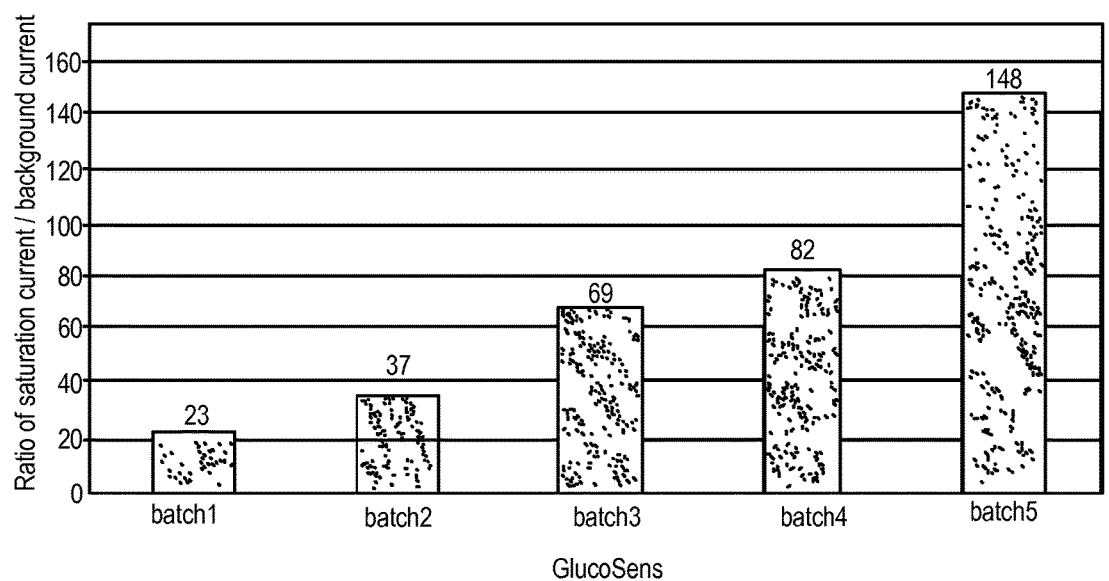

Referring now to FIG. 7, Q can be increased even further by optimizing the formulation of the paste for the hydrophilic such as using of a detergent as part of the hydrophilic membrane. The magnitude of the increase of course depends on the type of detergent used. The Q value for trips containing Triton or CHAPS are compared in FIG. 7. Using the zwitter-ionic detergent CHAPS in the hydrophilic membrane Q was increased by a factor of 1.5 in comparison to the non-ionic detergent Triton X IOO. Referring now to FIG. 8, further modifications of analyte detecting devices according to the present invention lead to ratios having values up to 148, though the detergent tends to be rather unstable. Different types of analyte detecting device constructions have given rise to different values of Q in FIG. 8.

Batch 1 is an analyte detecting device without membrane: similar to what is available in the art the resultant Q is 23. Batch 2 is an analyze detecting device constructed with the proprietary hydrophilic membrane, increasing to Q to 37. Batch 3 and 4 contain the hydrophilic membrane and different zwitterionic detergent compounds, resulting in almost double of the value for Q. Batch 5 is the highest operating Q value of about 150, but the detergent has proven to be rather unstable. In one embodiment, Q of the present invention is in the range of 60 80. 2)

In another embodiment, the present invention provides a method for manufacturing an analyte detecting device using screen printing a plurality of layers, such as but not limited to seven layers wherein adhesive is counted as one layer. Currently available glucose test strips have sample chambers created by laminating step.

Figure 9A:
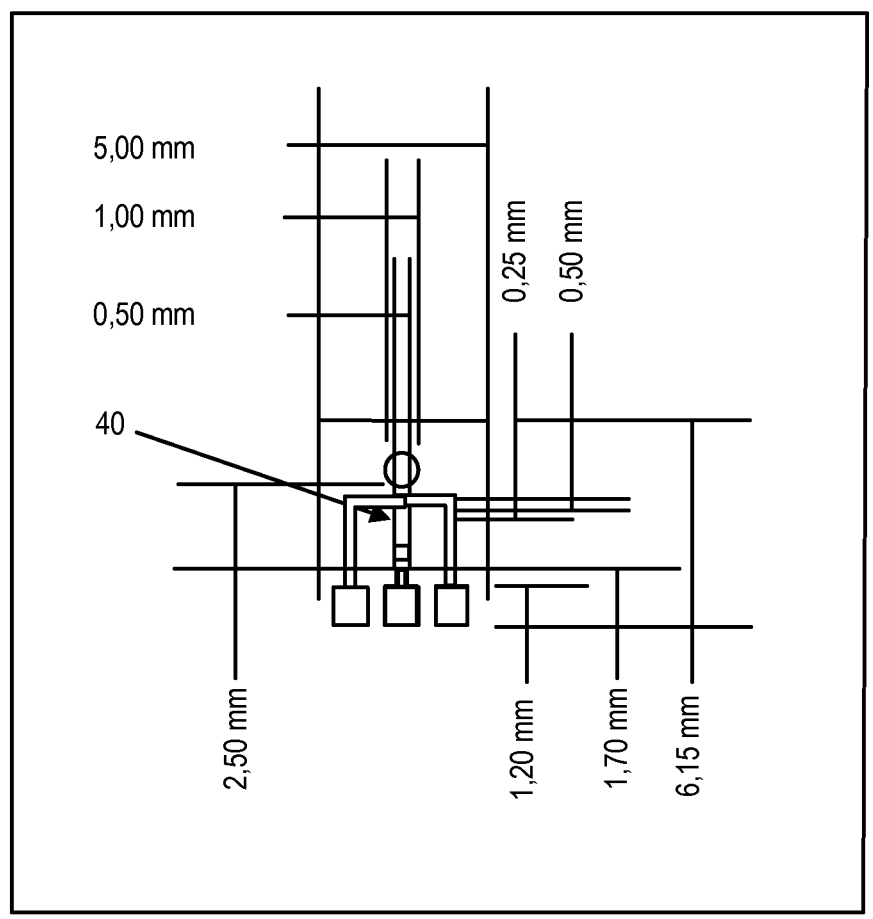
FIGS. 9(a) and 9(b) illustrate embodiments of a testing device according an embodiment of the present invention.
Figure 9B:
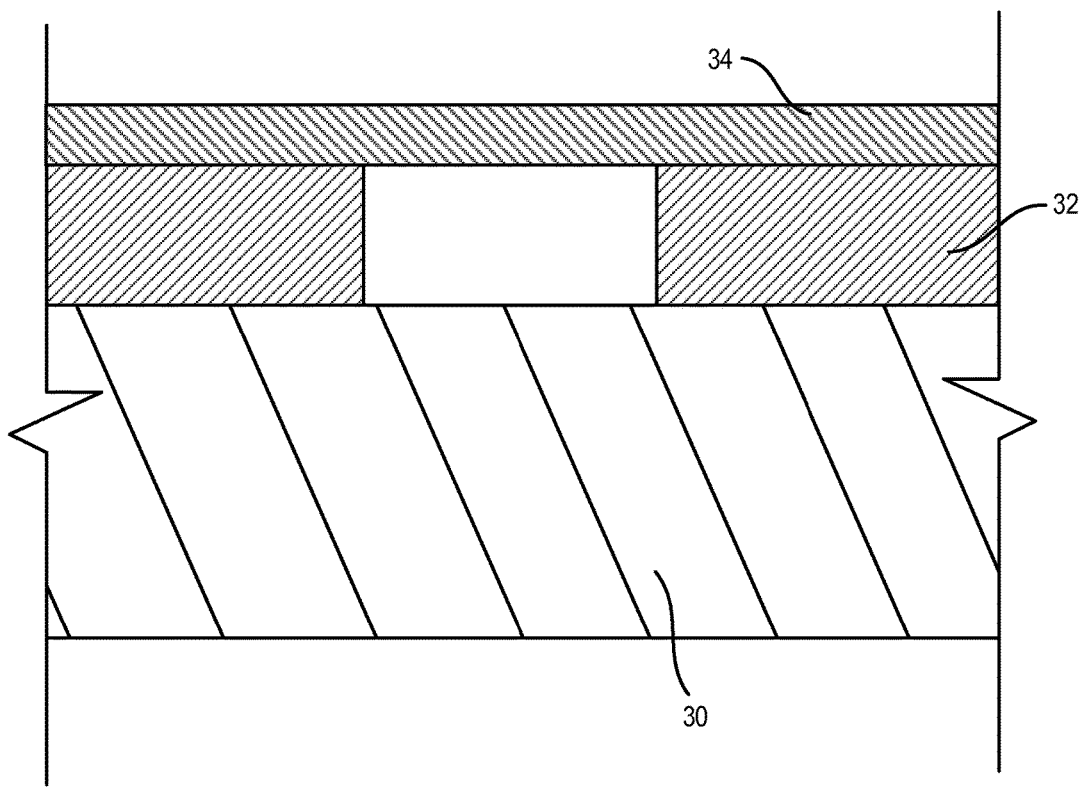

In one embodiment the analyte detecting structures of the present invention can be formed by laying the following layers. 1. Conductive layer 2. Insulating layer 3. Reference and counter electrode 4. WE 5. hydrophilic membrane 6, spacer layer 7 and adhesive layer. FIG. 9(a) illustrates dimension of the sample capturing structure without mesh (GS-SC 1, in its original form). The structure, in some other embodiments, can includes a mesh. By way of example and limitation, a channel 40 can have a width of 0.5 mm. The opening over each electrode is also about 0.5 mm. The contact pads can have a size of 1.2 mm. An opening can have a diameter of 1.0 mm. As seen in FIG. 9(b), one embodiment of the present invention comprises of six layers which can be manufactured by seven printing steps. In this method, five steps construct the electrode elements 30 while 2 steps account for the two layers 32 and 34 that comprise the microfilling features.

In one embodiment of the present invention, channels are printed that are used for hydrophilic filling. 30 µm2 printing is challenging but being done. In one embodiment, a 30 μm2×50 μm thick electrode would use 1 nl volume. In some embodiments of the present invention a sample volume of only 0.6 μL is required. In one embodiment, the noise floor issues mean that the lowest amperage for dilution can 10 nA. By way of illustration, and without limitation, the dimensions are 0.4 μL, 5 mm2×80 μm area×thickness. In one embodiment, 0.2 μL 4 mm2×50 μm=200 nA signal. In one embodiment, 1 mm2×100 μm=0.1 μL is challenging but doable for a 10 nA signal, the present invention could go 1/20 of the 0.2 μL. In one embodiment the present invention could theoretically do 0.1 mm2×0.05 μl or 0.005 μL 0.5 nl.

Figure 10:
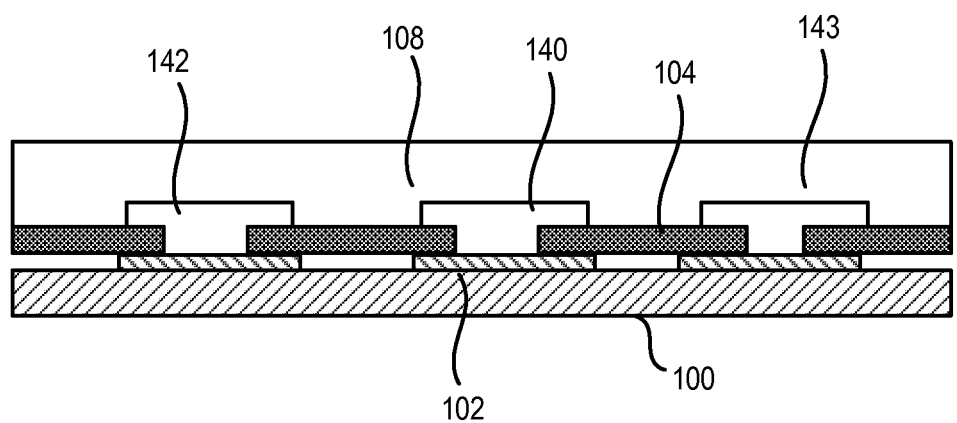
FIG. 10 is a cross-sectional view of one embodiment of the present invention.

Referring now to FIG. 10, an embodiment is illustrated connecting hydrophilic layer to the conductive layer. The "mushroom" shaped electrode can connect the conductive layer to the hydrophilic membrane with increased surface area using a drop through geometry. The mushroom shaped cap of the electrode is configured to increase the surface area in contact with the layer above.

FIG. 10 illustrates a cross-section of the analyte detecting members. In this embodiment a substrate 100 is provided. On top of this substrate, a carbon paste is provided to form conducting layers 102 for a screen-printed three-electrode system. A spacer layer 104 can also be provided. The reference and the counter electrodes 142 and 143 can be made of a formulation of Ag/AgCl. The analyte detecting member can be based on chrono-amperometry measurement technique using glucose oxidase (Gox) enzyme and N,N,N',N'-Tetramethyl-p-phenylenedianline (TMPD), as electron transfer mediator. Although not limited to the following, the working electrode 140 can optionally comprise of carbon paste blended with Gox, the mediator, a buffer and a thinner.

A hydrophilic layer or membrane 108 is provided on top of the electrodes. In some embodiments. only the working electrode 140 has the hydrophilic layer 108. It should be understood that the hydrogel can be formed in a variety of shapes including but not limited to rectangular, square, polygonal, circular, triangular, any single or multiple combination of shapes, or the like. Embodiments of the present invention can use a three electrode system. For testing devices with "bad" mediators, there is normally a dummy electrode, which is used to reduce background current. The reference electrode of the present invention is a more advanced design as it conveys the potential. It is independent of sample variability, so it achieves a constant potential between the working electrode and the counter electrode.

Figure 11A:
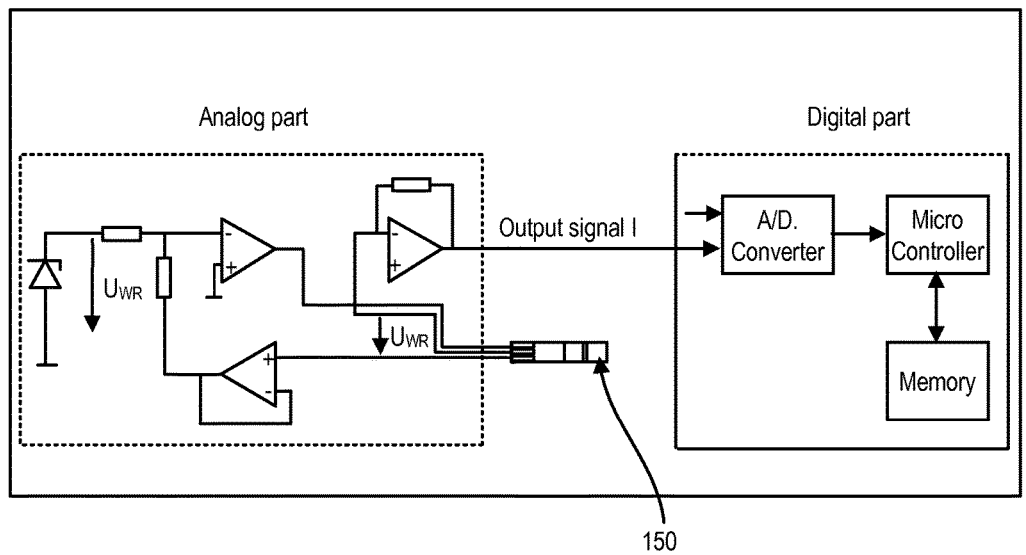
FIGS. 11(a) and 11(b) are schematics of electronic circuits according various embodiments of the present invention.

Referring now to FIG. 11(a), another embodiment of the present invention provides a meter relay 200 for sensing sample arrival and monitoring flow of sample in the testing device. In one embodiment of the present invention, FIG. 11(a) illustrates a system with electronics that do not handle switching and coupled to a testing device 150.

Figure 11B:
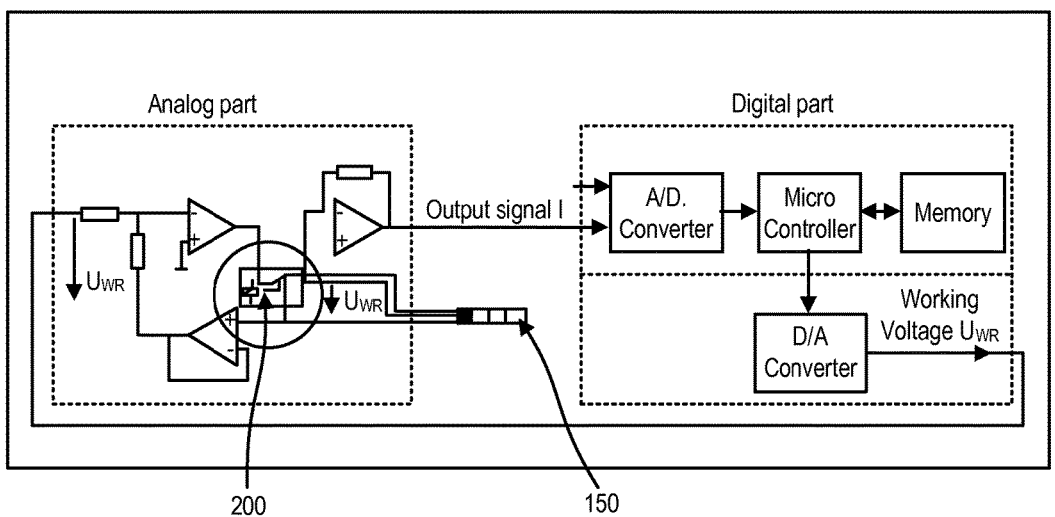

FIG. 11(b) illustrates a system with electronics that two of the electrodes can used for an auto-trigger function while all three electrodes can be used for the measurement FIG. 11(b) illustrates an analyte detecting device 150 coupled to a switch 200. In this embodiment, the switch is located in the analog portion of the meter electronics. Other embodiments can locate the switch in a digital part of the circuit A switch, relay or other type of general switch device can be used to switch monitoring of various electrodes. The switch 200 allows for monitoring of the first and second electrodes which contact the fluid sample. The switch 200 when moved into a second configuration allows for monitoring of the second and third electrodes in the testing device that contact tile fluid sample. The signal is transferred to tile digital portion 203 of the circuit which includes a microcontroller 205 for processing information from the various sets of electrodes.

Figures 12A, 12B:
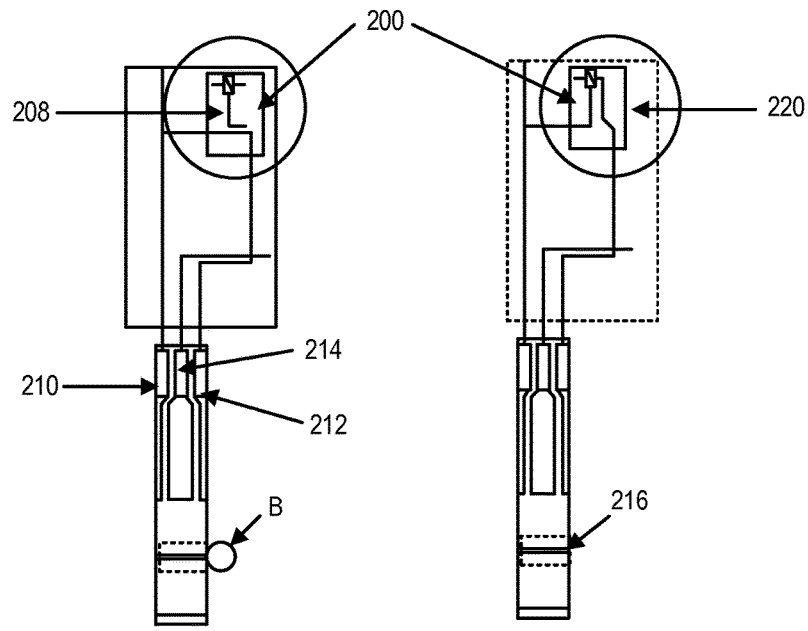
FIGS. 12(a) and 12(b) illustrate an embodiment of the present invention using as a switcher.

As seen in the embodiment of FIG. 12(a), in the start condition, the counter relay 200 is open as indicated by arrow 208. A reference electrode lead 210, counter electrode lead 212, and working electrode 214 lead is illustrated. As seen in FIG. 8, if the blood sample wets the reference electrode as indicated by arrow 216, the measurement starts in the two electrode-system modes until the current reaches the threshold level. Then in FIG. 12(b), the counter relays 200 closes as indicated by arrow 220 and the amperometric measurement for the detection of the glucose occurs in the three electrode system mode. Threshold level (value for auto trigger) is adjustable from 50 to 2,000 Na. Thus, a two electrode-system used for auto-trigger function, three electrode-system used for the measurement In summary, blood sample wets the reference electrode, the counter relays is switched, and the amperometric measurement starts.

In one embodiment, instead of measurement using the first two electrodes, the electrodes can also be used to monitor fluid flow in the capillary. As a non-limiting example, when blood covers the first electrode and contacts the second electrode, the signal begins to flow. The relay 200 then switches to monitor the time it takes for blood (after it contacts the second electrode, typically the working electrode) until the blood reaches the third electrode. The time it takes for the blood to flow from working electrode to the third electrode is monitored to know the flow velocity in the capillary. If the time it takes for blood to flow from the second to third electrode exceeds a threshold, then the measurement can be discarded. As a non limiting example, the threshold can be one minute, two minutes, or more.

Figures 13A, 13B, 13C:
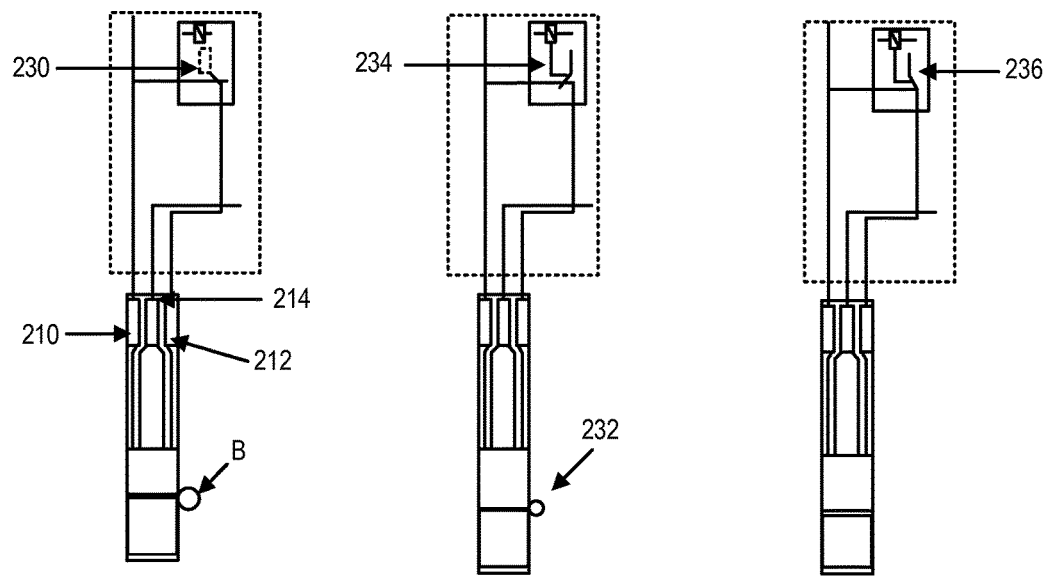
FIGS. 13(a)-13(c) illustrate another embodiment of the present invention using as a switcher.

Referring now to FIGS. 13(a)-13(c), another embodiment of the present invention will now be described. As indicated by arrow 230, in the starting condition, the counter array 200 is closed. If the blood sample B wets the working electrode as indicated by arrow 232 as seen in FIG. 13(b), a current is detected, a non-regulated potential. The relays are switched to the open modus as indicated by arrow 234. When a blood sample wets the working electrode, the counter relay is switched to the open modus. If the blood sample wets the reference electrode, the measurement starts in the two electrode-system mode until the current reaches the threshold level. The counter relay then closes, as indicated by arrow 236, and the amperometric measurement for the detection of the glucose occurs in the three electrode-system mode.

This feature provides the opportunity to measure the flow rate of the blood. This feature also permits the system to reload with more blood. However, if the time difference (current peak, if working electrode has been wet, and current peak, if reference electrode has been wet) is too long, the measurement is omitted (time control for reloading). As a non limiting example, the threshold level, value for auto trigger, can be adjustable from 50 to 2,000 nA. The threshold level is a compromise between possible non-fluid caused currents and the slope. Although blood is the example used wherein for illustrative purposes, it should be understood that other body fluids can be used, depending on the analyte being measured. When blood samples wet the reference electrode, the counter relay is switched to the closed modus and the amperometric measurement begins.

In certain embodiments, the present invention not only detects that the capillary is filled when blood reaches the third electrode, but it also monitors the movement of blood to and through the electrochemical cell or testing device. Detecting movement into and through the channel can have its benefits. In one embodiment, the present invention monitors the movement of the sample. This can be achieved with detecting the potential between two electrodes. There is a current flow when two electrodes are contacted by blood and a signal is generated. The potential is then between the two different electrodes, which allows current flow and a signal. The second signal illustrates that the capillary is filled. As discussed above, the present invention can use a switcher. A general switcher can be used to monitor two different locations. In this embodiment monitoring means determining the entry of the blood, when the capillary is filled, and thus the velocity of fluid flow. This is based on the time.

In one embodiment, the electrochemical cell starts when touch working electrode and when capillary is filled. In one embodiment, the partial covering of the working electrode and filling the whole channel are achieved. The allows the monitoring of blood through the sample device. A maximum time that is allowed to fill the whole channel can be determined.

Figure 14:
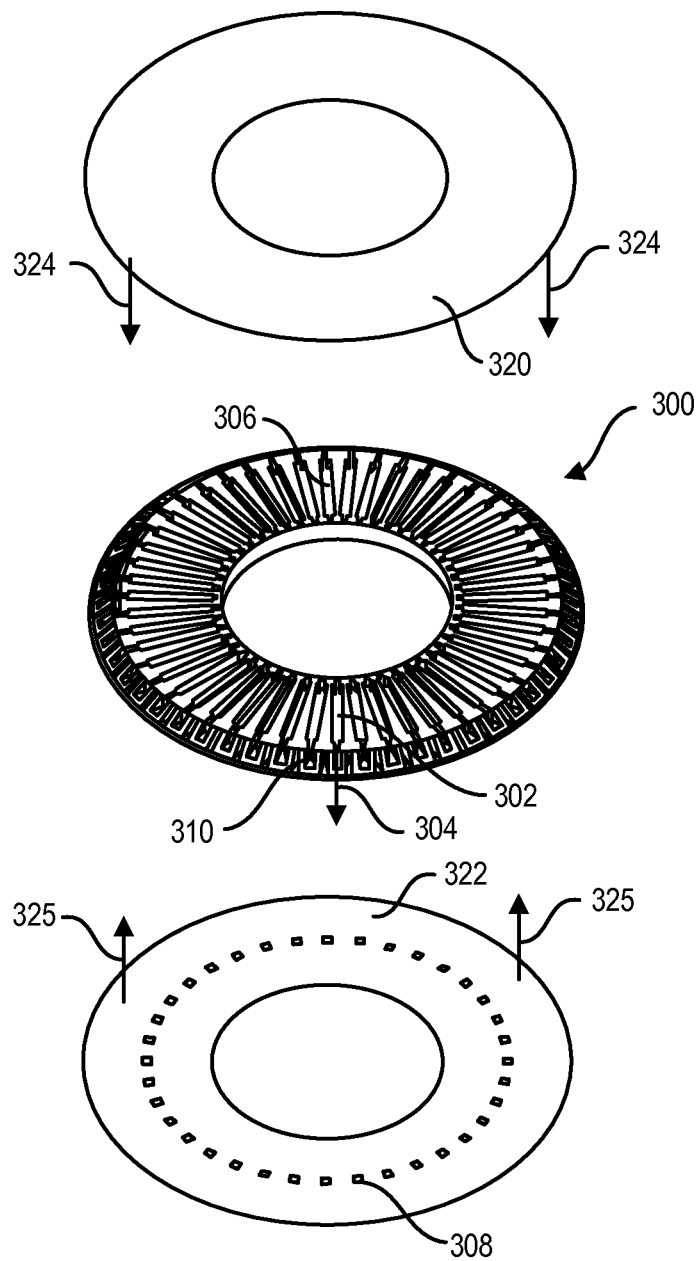
FIG. 14 illustrates one embodiment of a disc for use with the present invention.

FIG. 14 illustrates one embodiment of a cartridge 300 that can be removable inserted into an apparatus for driving penetrating members to pierce skin or tissue. The cartridge 300 has a plurality of penetrating members 302 that can be individually or otherwise selectively actuated so that the penetrating members 302 can extend outward from the cartridge, as indicated by arrow 304, to penetrate tissue. In the present embodiment, the cartridge 300 can be based on a flat disc with a number of penetrating members such as, but in no way limited to, (25, 50, 75, 100, . . . ) arranged radially on the disc or cartridge 800. It should be understood that although the cartridge 300 is illustrated as a disc or a disc-shaped housing, other shapes or configurations of the cartridge can also work without departing from the spirit of the present invention of placing a plurality of penetrating members to be engaged, singly or in some combination, by a penetrating member driver. Each penetrating member 302 can be contained in a cavity 306 in the cartridge 300 with tile penetrating member's sharpened end facing radially outward and can be in the same plane as that of the cartridge. The cavity 306 can be molded, pressed, forged, or otherwise formed in the cartridge. Although not limited in this manner, the ends of the cavities 306 can be divided into individual fingers, such as one for each cavity, on the outer periphery of the disc. The particular shape of each cavity 306 can be designed to suit the size or shape of the penetrating member therein or the amount of space desired for placement of the analyte detecting members 808.

As a non limiting example, the cavity 306 can have a V-shaped cross section, a U-shaped cross section, C-shaped cross-section, a multi level cross section or the other cross-sections. The opening 810 through which a penetrating member 302 exits to penetrate tissue can have a variety of shapes including but not limited to, a circular opening, a square or rectangular opening, a U-shaped opening, a narrow opening that only allows tile penetrating member to pass, an opening with more clearance on the sides, a slit or the other shapes. In this embodiment, after actuation, the penetrating member 302 is returned into the cartridge and can be held within the cartridge 300 in a manner so that it is not able to be used again.

By way of example and not limitation, a used penetrating member can be returned into the cartridge and held by the launcher in position until the next lancing event At the time of the next lancing, the launcher can disengage the used penetrating member with the cartridge 300 turned or indexed to the next clean penetrating member such that the cavity holding the used penetrating member is position so that it is not accessible to the user, e.g., turned away from a penetrating member exit opening.

In some embodiments, the tip of a used penetrating member can be driven into a protective stop that hold the penetrating member in place after use. The cartridge 300 is replaceable with a new cartridge 300 once all the penetrating members have been used or at such other time or condition as deemed desirable by the user. I S Referring still to the embodiment in FIG. 14, the cartridge 300 can provide sterile environments for penetrating members via seals, foils, covers, polymeric, or similar materials used to seal the cavities and provide enclosed areas for the penetrating members to rest in. In the present embodiment, a foil or seal layer 320 is applied to one surface of the cartridge 300. The seal layer 320 can be made of a variety of materials such as a metallic foil or other seal materials and can be of a tensile strength and other quality that can provide a sealed, sterile environment until the seal layer 320 is penetrate by a suitable or penetrating device providing a preselected or selected amount of force to open the sealed, sterile environment.

In one embodiment, each cavity 306 can be individually sealed with a layer 320 in a manner such that the opening of one cavity does not interfere with the sterility in an adjacent or other cavity in the cartridge 800. As seen in the embodiment of FIG. 14, the seal layer 320 can be a planar material that is adhered to a top surface of the cartridge 800. Depending on the orientation of the cartridge 300 in the penetrating member driver apparatus, the seal layer 320 can be on the top surface, side surface, bottom surface, or other positioned surface" For ease of illustration and discussion of the embodiment of FIG. 14, the layer 320 is placed on a top surface of the cartridge 800" The cavities 306 holding the penetrating members 302 can be sealed on by a seal layer 320 and thus create the sterile environments for the penetrating members. The seal layer 320 can seal a plurality of cavities 306 or only a select number of cavities as desired.

In one embodiment, illustrated in FIG. 14, tile cartridge 300 can optionally include a plurality of analyte detecting members 308 on a substrate 822 which can be attached to a bottom surface of the cartridge 300" The substrate can be made of a material such as, but not limited to, a polymer, a foil, or other material suitable for attaching to a cartridge and holding the analyte detecting members 308"

The substrate 322 can fold a plurality of analyte detecting members, including but not limited to about, 10 50, 50100, or other combinations of analyte detecting members. This facilitates the assembly and integration of analyte detecting members 308 with cartridge 300. These analyte detecting members 308 provide an integrated body fluid sampling system where the penetrating members 302 create a wound tract in a target tissue that spontaneously expresses body fluid that flows into the cartridge for analyte detection by at least one of the analyte detecting members 308.

The substrate 322 can contain any number of analyte detecting members 308 suitable for detecting analytes in cartridge having a plurality of cavities 306. In one embodiment, many analyte detecting members 308 are printed onto a single substrate 322 which is then adhered to the cartridge to facilitate manufacturing and simplify assembly. The analyte detecting members 308 can be electrochemical in nature. The analyte detecting members 308 can further contain enzymes, dyes, or other detectors which react when exposed to tile desired analyte.

Additionally, the analyte detecting members 308 can have clear optical windows that allow light to pass into the body fluid for analyte analysis. The number, location, and type of analyte detecting member 308 can be varied as desired, based in part on the design of the cartridge, number of analytes to be measured, the need for analyte detecting member calibration, and the sensitivity of the analyte detecting members. If tile cartridge 300 uses an analyte detecting member arrangement where the analyte detecting members are on a substrate attached to the bottom of the cartridge, through holes, as illustrated in FIG. 11, wicking elements, capillary tube or other devices can be provided on the cartridge 300 to allow body fluid to flow from the cartridge to the analyte detecting members 308 for analysis.

In some embodiments, the analyte detecting members 308 can be printed, formed, or otherwise located directly in the cavities housing the penetrating members 302 or areas on the cartridge surface that receive blood after lancing. The use of the seal layer 320 and substrate or analyte detecting member layer 822 can facilitate the manufacture of these cartridges I 0. For example, a single seal layer 320 can be adhered, attached, or otherwise coupled to the cartridge 300 as indicated by arrows 324 to seal many of the cavities 306 at one time. A sheet 322 of analyte detecting members can also be adhered, attached, or otherwise coupled to the cartridge 300 as indicated by arrows 325 to provide many analyte detecting members on the cartridge at one time.

As a non-limiting example, during manufacturing of one embodiment of the present invention, the cartridge 300 can be loaded with penetrating members 302, sealed with layer 320 and a temporary layer (not illustrated) on the bottom where substrate 322 would later go, to provide a sealed environment for the penetrating members. This assembly with the temporary bottom layer is then taken to be sterilized. After sterilization, the assembly is taken to a clean room, or it can already be in a clear room or equivalent environment, where the temporary bottom layer is removed and the substrate 322 with analyte detecting members is coupled to the cartridge as illustrated in FIG. 14. This process allows for the sterile assembly of the cartridge with the penetrating members 302 using processes and/or temperatures that can degrade the accuracy or functionality of the analyte detecting members on substrate 322.

As a non-limiting example, the entire cartridge 300 can then be placed in a further sealed container such as a pouch, bag, plastic molded container, and the like, to facilitate contact, improve ruggedness, and/or allow for easier handling" In some embodiments, more than one seal layer 320 can be used to seal the cavities 306. As examples of some embodiments, multiple layers can be placed over each cavity 306, half or some selected portion of the cavities can be sealed with one layer with the other half or selected portion of the cavities sealed with another sheet or layer, different shaped cavities can use different seal layer, or the like. The seal layer 320 can have different physical properties. In one embodiment, the seal layer covering the penetrating members 302 near the end of the cartridge can have a different color to indicate to the user that the number of penetrating members is running low.

Figure 15:
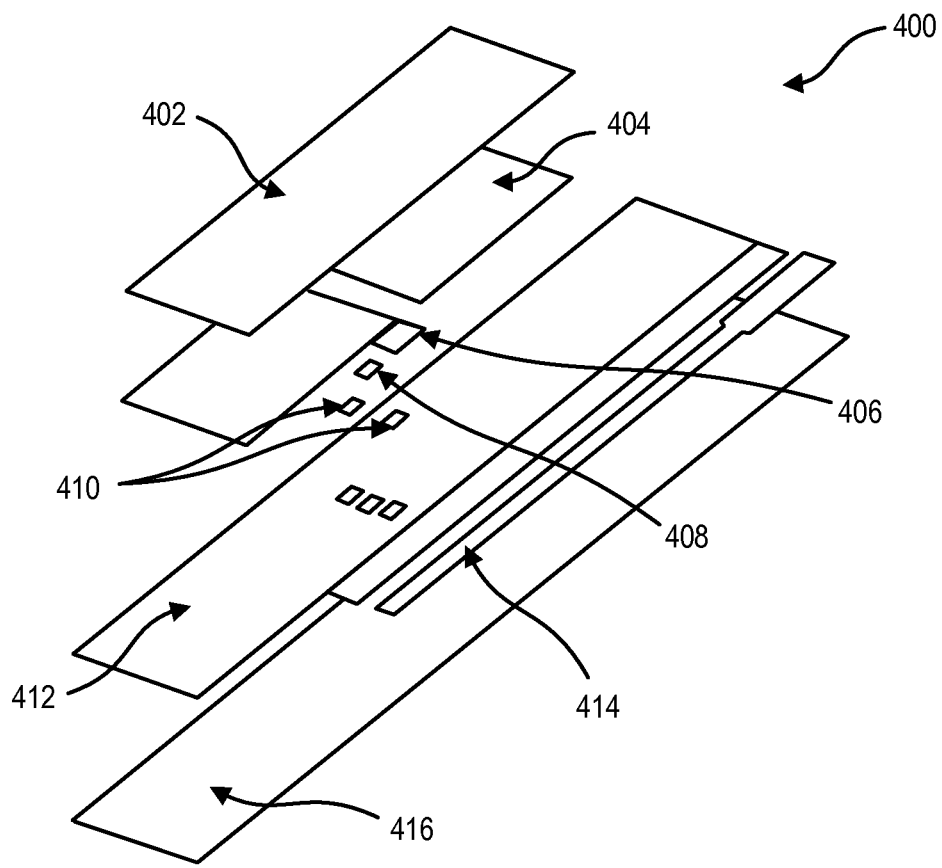
FIG. 15 is an exploded perspective view of one embodiment according to the present invention.

As illustrated in FIG. 15, device 400 is illustrated in an exploded view. In this embodiment device 400 includes a hydrophilic cover 402, spacer 404, hydrophilic member 406, working electrode 408, counter and reference electrodes 410, insulating layer 412, conductive lines 414, and a substrate 416. The analyte detecting members can be printed in sheets. From the sheets the analyte detecting members are placed at high density in concentric rings or other configurations, including but not limited to lines, linear arrays, circular arrays, square arrays, polygonal arrays, triangular arrays, and the like, on the disk.

Figure 16:
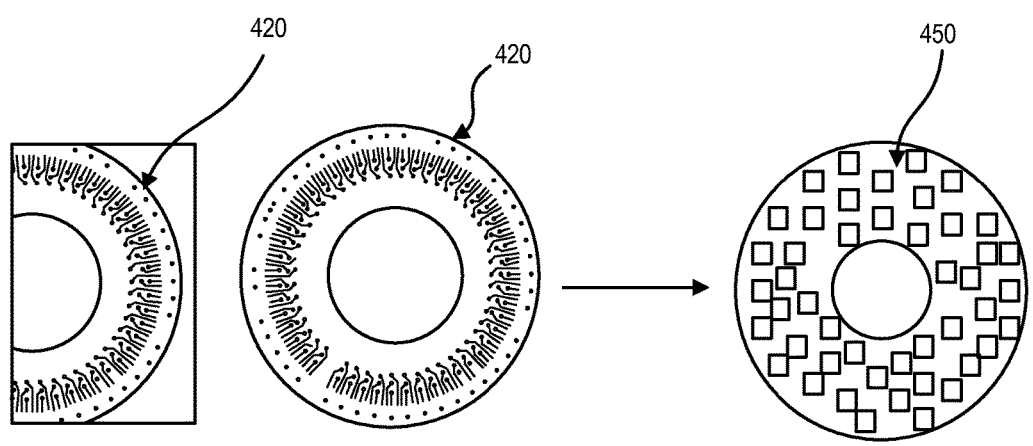
FIG. 16 illustrates a ring according to an embodiment of the present invention.

Referring now to the FIG. 16 embodiment, the analyte detecting members 420 are positioned in the arrays on sheets at high density. In one embodiment high density manufactured analyte detecting members are die cut and placed on the ring 450. The density of the analyte detecting members is increased by adhering the analyte detecting members in consecutive rings that diminish in size as the diameter decreases, going from the outside to the inside of the ring. This can decreases manufacturing cost 12 fold in comparison to GSD. As a non-limiting example, in this embodiment the printed areas can be 150 sq mm compared to 1875 sq mm for GSD.

Desiccant can also be printed in a paste that forms a microfluidic channel. This reduces additional packaging. As a non-limiting example, the desiccant can be a desiccant-coated AI film In another embodiment, illustrated in FIG. 17, an analyte detecting member disc 580 can be mounted to position analyte detecting members 590 on an outside rim of the cartridge 600 housing. At least one penetrating member 602 is provided. In some embodiments, a hydrophilic cover member 604 can be included. In the FIG. 17 embodiment, analyte detecting can be accomplished using a film mesh 610 at a front end to draw blood to tile analyte detecting members 590. The film mesh 610 can be advanced after use to provide a fresh piece for every test. In the FIG. 17 embodiment, the cartridge 600 and analyte detecting member disk 580 are the same, contamination is reduced and/or eliminated, analyte detecting member-analyte detecting member-isolation is achieved due to tile hydrophilic cover film and analyte detecting member and penetrating member isolation is achieved.

In one embodiment, contact to tile meter is easily achieved through pins to establish electrical contact between conductive lines coupled to members 590 and the meter (not illustrated). A vent can be created at a beginning of measurement by using a needle to pierce a hole through the film at the end of the capillary. A penetrating member exit point can be through a center of the film mesh 610. In one embodiment, a new indexing mechanism is provided to move the disc in addition to the cartridge 600. This provides dull rotation and indexing and allows for an increase in the density of the analyte detecting members. As a non-limiting example, one analyte detecting disc can be used for every two penetrating member cartridges. Additionally precise film transportation can be used.

Figure 18:
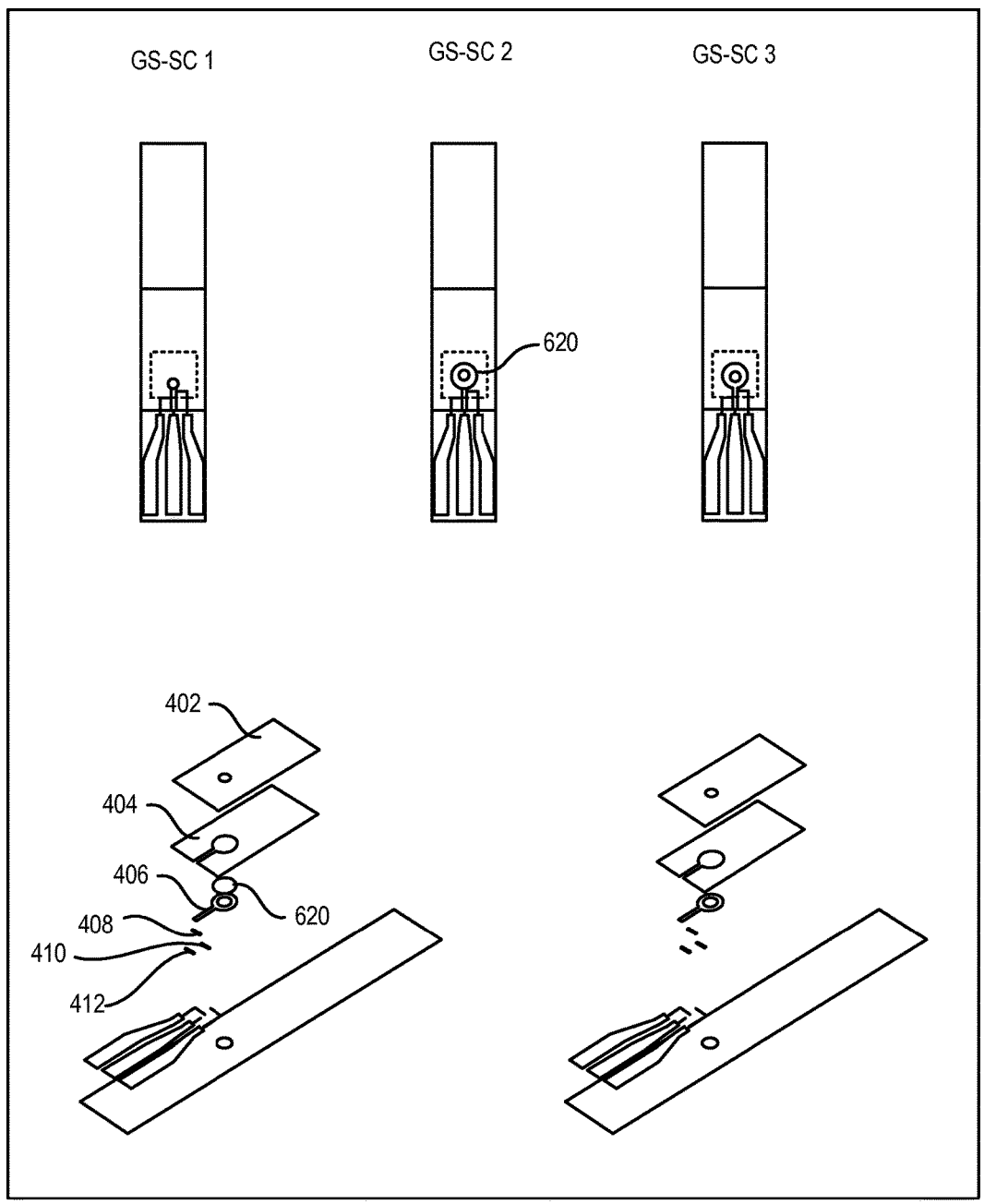
FIG. 18 illustrates several embodiments according to the present invention.

In another embodiment, illustrated in FIG. 18, tile height of the channel is decreased to decrease the volume of blood or fluid sample. As a non-limiting example, tile height of the channel is decreased and the volume of fluid sample was dropped to 0.2 µl from a starting sample volume of 0.6 µL. As non-limiting examples, (i) the height of tile channel can be about 50 am and (ii) tile length of the channel is reduced and the height increased to 80 am which minimizes problems of high Haematocrit or viscosity. As a non limiting example" the sample volume is OA µL" width of the channel is 500 am by masking, the channel has a length of 1 000 am, 4 layers above the electrode are aligned, the working electrode is 2000 µm and has a 500 am gap. As a non-limiting example, the size of the sample capturing structure in its original form is 6.15 mm×5 mm (without mesh, see FIG. 5A, as well as 7.75 mm×5 mm (with mesh).

FIG. 18 illustrates an overview of tile three different variants of sample capturing structures that has an enlarged structure.

Figure 17:
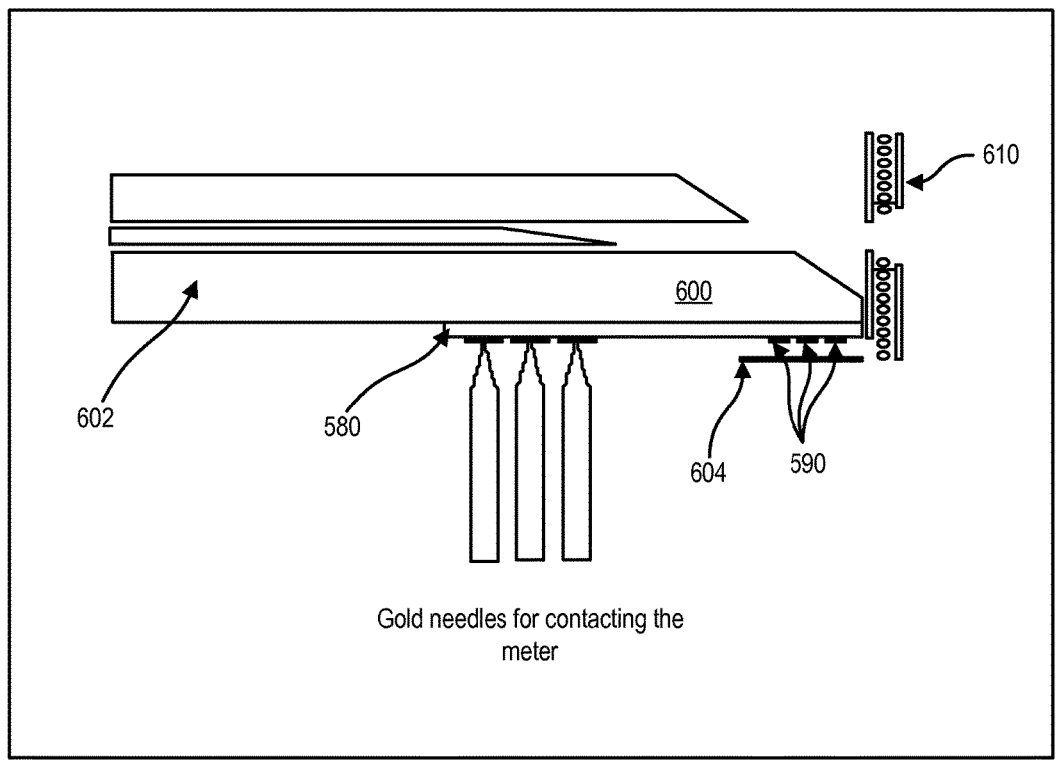
FIG. 17 illustrates a cross-sectional view of one embodiment of the present invention.

Referring to FIG. 17, in various embodiments dimensions of different layers and structures are as follows: (i) GS-SC 1 does not have a mesh 620 and both apertures have a diameter of 1 mm, (ii) GS-SC 2 has a mesh 620, the aperture diameter in the cover film is 1 mm, the aperture diameter in the PVC support is 1.6 mm" and the aperture diameter in the PSA layer is 2.6 mm and (iii) GS-SC 3 without the mesh 620, has an aperture diameter in the cover film of 1 mm, an aperture diameter in PVC support of 1.6 mm, and an aperture diameter of the PSA layer of 2.6 mm.

EXAMPLE 2

Example 2 discloses one embodiment for manufacturing analyte detecting devices, more particularly electrode elements, of the present invention. It is intended to be illustrative of an embodiment, and is a non-limiting example. Tile batch size can be 10 sheets and include, (i) drilling apertures into PVC-support, (ii) printing conductive lines and control of the resistance, (iii) printing of the insulating layer, (iv) printing reference and counter electrodes, (v) printing the working electrode (Composition: 50%, mediator/100% buffer compounds/50'%. GOD), (vi) printing the hydrophilic membrane (Composition: PAA/CHAPS), (vii) printing the spacer layer In process-control with measurement of background and saturation current, (viii) printing the PSA-layer, (ix) applying the mesh (for the mesh structure) and (x) applying the cover film 126 with two apertures. A stamping process for electrochemical characterization of analyte detecting devices can include determination of background and saturation current (n=24 48).

Measurements were taken during tile maturation process, up to 3-4 weeks, directly after the maturation process and over a long period following the maturation process. Determination of KM as well as determination of the slope within the linear range 1, 2, 3, 4, 5, 6, 7, 8, 9, 10, 12, 15, 20, 25, 50, 100, 200, 300, 400, 500 mM glucosein buffer 20 different glucose solutions, was done with measurement per concentration: n=8. Measurement of 40 different blood samples was performed covering a glucose range from 1 to 40 mM glucose, measurement per concentration: n=8 Evaluation. Error Grid Analysis was performed by applying tile samples with a pipetman and applying of the samples with finger.

While the invention has been described and illustrated with reference to certain particular embodiments thereof, those skilled in the art will appreciate that various adaptations, changes, modifications, substitutions, deletions, or additions of procedures and protocols can be made without departing from the spirit and scope of the invention

REFERENCES

The following references are incorporated herein by reference:
Adolphe X., Martemianov S., Palchetti l., Mascini M., (2005) "On the electrochemical flow measurements using carbon-based screen-printed electrodiffusion probes" *Journal of Applied Electrochemistry* 35:599-607; Jung et al. (1998), "Electrodes for electrochemical cells and method of making same" U.S. Pat. No. 5,728,181;
Jarzqbek G., Borkowska Z., (1997). "On the real surface area of smooth solid electrodes.", *Electrochimica Acta,* 42(19): 2915-2918; Trasatti S., Petri A., (1991) "Real surface measurements in electrochemistry" *Pure & Appl. Chem.,* 63, (5): 71-734, 1991; www.pineinst.com/echem. Accessed on Mar. 5, 2008. http://www.babylon.com/definition/chronocoulometry/English. Accessed on Mar. 5, 2008.

Batt A. W., Heineman W. R., (2004), "Chronocoulometry.", *Current Separations,* 4(20): 121-126; http://www-.chem.uic.edu/chem222su05/pdf/5/StAdlnt.pdf Accessed on Mar. 5, 2008; and E. T. Pawner, F. Yalcinkaya, (1997), "Intelligent biosensors", *Sensor Review,* 17(2):107-116.

Expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A method for sensing arrival and monitoring flow of a sample in a testing device, comprising:
providing a meter relay for sensing a sample arrival in the testing device that includes three electrodes for measurement of an analyte in a sample that includes a switch located in an analog or digital part of a circuit, the testing device including a reference electrode lead, a counter electrode lead, and a working electrode, the metal including a cartridge positionable in the testing device and a disc,
in a start condition having a counter relay open;
using first and second electrodes in an auto-trigger function;
starting a measurement when the sample wets the second electrode until a current reaches a threshold level of from 50 to 2,000 Na;
closing counter relays for the testing device when a threshold level is reached; and
providing a dual rotation and indexing of the disc and the cartridge.

2. The method of claim 1, wherein the sample is a blood sample.

3. The method of claim 1, wherein the measurement of the analyte is an amperometric measurement.

4. The method of claim 1, wherein the threshold level is the value for the auto trigger function to start.

5. The method of claim 1, wherein the threshold level is adjustable.

6. The method of claim 1, wherein the switch provides for monitoring of the first and second electrodes which contact with the sample.

7. The method of claim 1, further comprising:
moving the switch to a second configuration for measuring an amount of the analyte with the second and third electrodes.

8. The method of claim 1, further comprising:
monitoring the second and third electrodes in the testing device in the second configuration.

9. The method of claim 8, further comprising:
producing a signal in the second configuration that is indicative of an amount of the analyte.

10. The method of claim 9, further comprising:
transferring the signal to a digital portion of the circuit which includes a microcontroller.

11. The method of claim 1, further comprising:
using a relay to switch to monitor a time it takes for the sample, after it contacts the second electrode until the sample reaches the third electrode.

12. The method of claim 11, further comprising:
using a time it takes for the sample to flow from the second electrode to the third electrode to determining a flow velocity of the sample.

13. The method of claim 12, further comprising:
discarding the measurement when the flow velocity exceeds a threshold, then the measurement can be discarded.

14. The method of claim 1, wherein the threshold is at least one minute.

\* \* \* \* \*